United States Patent [19]

Cannell et al.

[11] 4,174,952
[45] Nov. 20, 1979

[54] IMMUNOASSAY BY LIGHT SCATTERING INTENSITY ANISOTROPY MEASUREMENTS

[75] Inventors: David S. Cannell, Santa Barbara, Calif.; Marzio Giglio, Milan, Italy; George B. Benedek, Belmont, Mass.; Gustav K. von Schulthess; Richard J. Cohen, both of Brookline, Mass.

[73] Assignee: Massachusetts Institute of Technology, Cambridge, Mass.

[21] Appl. No.: 871,294

[22] Filed: Jan. 23, 1978

[51] Int. Cl.² .................. G01N 21/24; G01N 33/16
[52] U.S. Cl. .................. 23/230 B; 23/915; 356/341; 422/73; 250/574; 424/12; 435/7
[58] Field of Search .................. 23/230 B; 424/12; 250/574; 356/103, 104, 337, 341, 336; 195/103.5 A

[56] References Cited

U.S. PATENT DOCUMENTS

| 2,666,355 | 1/1954 | Trurnit | 424/12 X |
|---|---|---|---|
| 2,816,479 | 12/1957 | Sudan | 356/104 X |
| 3,310,680 | 3/1967 | Hasegawa | 356/104 |
| 3,653,767 | 4/1972 | Lisowitz | 356/104 X |
| 3,705,771 | 12/1972 | Friedman et al. | 356/104 X |
| 3,758,787 | 9/1973 | Sigrist | 356/104 X |
| 3,824,402 | 7/1974 | Mullaney et al. | 250/574 X |
| 3,905,767 | 4/1975 | Morris et al. | 23/230 B |
| 3,942,897 | 3/1976 | Takahashi et al. | 356/104 X |
| 3,967,901 | 7/1976 | Rodriguez | 250/574 |
| 3,984,533 | 10/1976 | Uzgiris | 424/12 |
| 3,990,851 | 11/1976 | Gross et al. | 424/12 X |
| 4,011,044 | 3/1977 | Uzgiris | 23/230 B |
| 4,078,863 | 3/1978 | Eriksson et al. | 356/104 |
| 4,080,264 | 3/1978 | Cohen | 424/12 X |
| 4,097,149 | 6/1978 | Aladjem et al. | 356/341 X |

OTHER PUBLICATIONS

Tengerdy et al.; Reaction Kinetic Studies of the Antigen–Antibody Reactor, Nature, 5/14/66, pp. 208–210, vol. 210.

Primary Examiner—Michael S. Marcus
Attorney, Agent, or Firm—Arthur A. Smith, Jr.; Paul J. Cook

[57] ABSTRACT

Method and apparatus for determining the concentration of any of a wide range of antigen or antibody molecules with a high degree of specificity, accuracy and sensitivity. Antigen or antibody concentration is determined by effecting an agglutination reaction between carrier particles in a liquid medium, exposing the liquid medium to a beam of light, and measuring the ratio of the intensities of light scattered at two different angles as a function of antigen or antibody concentration. The unknown concentration of antibody or antigen is determined by comparison with similar measurements of the anisotropy ratio using known concentrations of the molecule being tested for. The agglutination reaction is performed using carrier particles coated with an agglutinant. The carrier particles should be fairly uniform in size and their diameter can be less than or comparable to the wavelength of light. By this invention, one may specifically ascertain the absolute concentration of the antigen or antibody in question in the sample being analyzed. In addition to detecting antigen or antibody molecules, the process of this invention can be used to determine the concentration of any substance capable of specifically promoting or inhibiting an agglutination reaction.

5 Claims, 3 Drawing Figures

IMMUNOASSAY BY LIGHT SCATTERING INTENSITY ANISOTROPY MEASUREMENTS

BACKGROUND OF THE INVENTION

The Government has rights in this invention pursuant to Contract No. 5-P01-HL-14322-04 awarded by the Department of Health, Education and Welfare and Grant No. DMR72-03027-A05 and IPA-0010 awarded by the National Science Foundation.

This invention relates to a process for determining the concentration of substances capable of promoting or inhibiting agglutination reactions of carrier particles and agglutinants. The degree of agglutination is determined by measuring the ratio of the intensities of light scattered through two different angles by the agglutinated reaction product.

Agglutination reactions are widely used in biology and medicine to detect small quantities of antigen or antibody molecules. Agglutination reactions usually involve the in vitro aggregation of microscopic carrier particles which bear on their surface antigens or haptenes. Aggregation occurs when antibody molecules specifically corresponding to the antigen or haptene are introduced into the solution of the carrier particles. The converse procedure of agglutinating antibody-coated particles with the appropriate polyhaptenic antigen molecules is also used. Some of the carrier particles which have been used are red blood cells, bacteria and polystyrene spheres. At low concentrations of the agglutination-inducing antibody or antigen (henceforth termed the agglutinator), small aggregates consisting of only a few carrier particles are formed. At higher concentrations of agglutinator, the aggregates grow so large as to form visible clumps.

Conventionally, the appearance of this visible agglutinate has been taken as the criterion for the presence of the agglutinator. Clearly, this detection criterion suffers from several defects. First, the formation of the grossly visible agglutinate requires a much larger concentration of agglutinator than needed to form small microscopic aggregates. Moreover, whereas the reversible formation of small aggregates is a specific and reproducible process, the appearance of macroscopic agglutinates is subject to many poorly controlled influences, such as the presences of foreign surfaces. In addition, the appearance of a grossly visible agglutinate is so qualitative a criterion that it is difficult experimentally to determine quantitatively the associated agglutinator concentration. Conventionally, the agglutinator concentration is determined by preparing a serial dilution of the agglutinator-containing solution. Then an aliquot of each dilution is mixed with a fixed amount of carrier particles, and the highest degree of dilution which still permits the formation of a visible agglutinate is noted. (Henceforth all the reagents, including carrier particles, used in fixed amounts will be collectively termed the agglutinant). This serves to indicate the concentration of agglutinator in the original solution. The agglutinator concentration can at best be determined to within a factor of two by this method.

Thus, while the agglutination reaction, as conventionally performed, serves as a specific and versatile means of detecting antigen or antibody, it is severely limited in its application in that: (1) the process is not capable of providing an accurate quantitative measurement of either antigen or antibody concentrations and (2) the process may only be used for determining antibody concentrations which are sufficiently high so as to induce (or inhibit) macroscopically visible agglutination.

A presently available alternative method for determining antigen concentration is the radio immunoassay. In this method, a sample containing an unknown concentration of antigen is mixed with a fixed amount of antibody and a fixed amount of the antigen which has been radioactively labeled, usually with radioactive iodine. After separation of the bound antigen from the free antigen, the relative proportion of the bound and free antigen is determined by measuring the radioactivity of the two fractions or by difference. Similar measurements are made using known concentrations of the antigen being tested for. By comparison, the unknown antigen concentrations can be determined.

While this method is much more sensitive than the method for visually determining agglutination reaction precipitate, it has some disadvantages. The labeling process presents a radiation hazard and requires expensive shielding. Moreover, the labeled compounds are unstable and must be frequently prepared. Therefore, as a practical matter, the use of radioisotopes is expensive, difficult and hazardous, so that in many applications the radio immunoassay may not be used. In addition, the radio immunoassay is not generally used for the measurement of antibody concentrations, and thus, is undesirably limited to determining antigen concentrations.

Also, it has been proposed by Marrack, et al., Immunology, Vol. 20, pp. 1019–1040 (1970) and Blume, et al., Clinical Chemistry, Vol. 21, No. pp. 1234–1237 (1975) to determine the degree of agglutination of an antigen-antibody system by exposing the system to a light beam and measuring the intensity of scattered light. In the process of Blume, et al., the angular distribution of the light scattered by agglutinated particles exhibits a series of maxima and minima as a function of the scattering angle. Blume, et al. disclose that when aggregation starts, the first maximum becomes less pronounced and eventually merges into the shoulder of the large forward scattering lobe. In order to quantify this effect, plots are made of the scattered intensity as a function of the scattering angle and the slope of the curve then is calculated at a point intermediate between the first minimum and the first maximum. Plots of the slope versus dilution then are constructed and used to assay the antibody concentration.

One of the difficulties of the technique of Blume, et al. is that it capitalizes on the existence of a small, but supposedly well-defined, dip on the side of the main lobe when the sample is not aggregated. However, such a fine detail can be easily washed out by a modest initial polydispersity of the latex particles. Indeed, the authors explicity state that in 11 cases out of 85, their technique classified as positive, samples which were given as negative by the conventional technique (slide or tube agglutination test). In 7 other cases, the technique described by Blume, et al. failed to identify samples which were given as positive by the conventional technique. This is an indication that the technique is fairly unreliable and insensitive. Finally, the apparatus described by Blume, et al. is rather complex, since it involves an elaborate mechanical setup with moving parts, it requires a plotter, and the data handling is not straightforward.

Marrack, et al. disclose a method for determining the degree of agglutination of an antigen-antibody mixture without the aid of carrier particles. Since the antibody-antigen complex is quite small compared with the wavelength of light, there is very little change in angular anisotropy of the scattered light associated with the early stages of antigen-antibody complex formation. Furthermore, under normal conditions, the samples to be assayed contain a variety of proteins in addition to the antibody or antigen being assayed. The scattering from these proteins can effectively mask the changes associated with antibody-antigen complex formation.

Wyatt, et al. (J. Agric. Food Chem., Vol. 24, No. 5, 1976, p. 984) have described a means of assaying for drugs by means of the effect that the drug has on the angular distribution of the intensity of light scattered from a solution of bacteria sensitive to the drug. This technique does not involve agglutination of the bacteria, nor are the bacteria in any manner used as carrier particles. Their technique relies on measuring the entire angular distribution of the scattered intensity, and using a computer to process the resulting information. Since bacteria which are sensitive to any given drug suffer changes in size, shape, and number density upon exposure to the drug, the resulting light scattering pattern also changes, often in a complicated manner. These changes in the light scattering pattern can be used to assay for drugs or chemicals which affect the bacteria. It should be noted that this technique does not involve the use of either antigens or antibodies specific to some particular antigen, it does not involve an agglutination reaction, it is complicated and it is essentially limited to assaying for drugs rather than for the entire range of biological molecules capable of eliciting an immune response in some species.

Measurement of the ratio of intensity of light scattered at two different angles offers substantial advantages over the prior art methods consisting of intensity measurements at a single angle (e.g. nephelometry). The anisotropy ratio is a measure of the relative distribution of carrier particle aggregates and is not a measure of absolute carrier particle polymer concentrations as are the single angle scattering methods. Thus, the process of this invention is insensitive to such poorly controlled factors such as inadvertant loss of carrier particles on foreign surfaces and/or the precipitation of polymers from solution. The anisotropy ratio is independent of the absolute concentration of carrier particles. Also, the anisotropy ratio is a more sensitive measure of the agglutination process than a single scattering angle measurement, because it reflects both the increase in forward scattering and reduction in backward scattering caused by the agglutination.

SUMMARY OF THE INVENTION

This invention provides a means for specifically and quantitatively determining antigen or antibody concentration. An agglutination reaction between carrier particles coated with antibody or antigen is effected by the introduction of an agglutinator consisting of the complementary antigen or antibody. The early stages of the agglutination reaction are detected by measuring the ratio of the intensities of light scattered at two different angles by the agglutinated reaction product. One establishes a standard quantitative relationship between the measured anisotropy ratio and the agglutinator concentration. The resulting standard relationship is called the standard agglutination curve. The unknown concentration of agglutinator in the sample to be assayed for is determined by measuring the anisotropy ratio for the unknown sample and comparing it with the standard agglutination curve. In addition to determining the concentration of antigen or antibody molecules, the process of this invention can be used to determine the concentration of any substance capable of specifically promoting or inhibiting an agglutination reaction even when the formation of antigen-antibody bonds is not involved in the agglutination process.

DESCRIPTION OF SPECIFIC EMBODIMENTS

Figure 3:
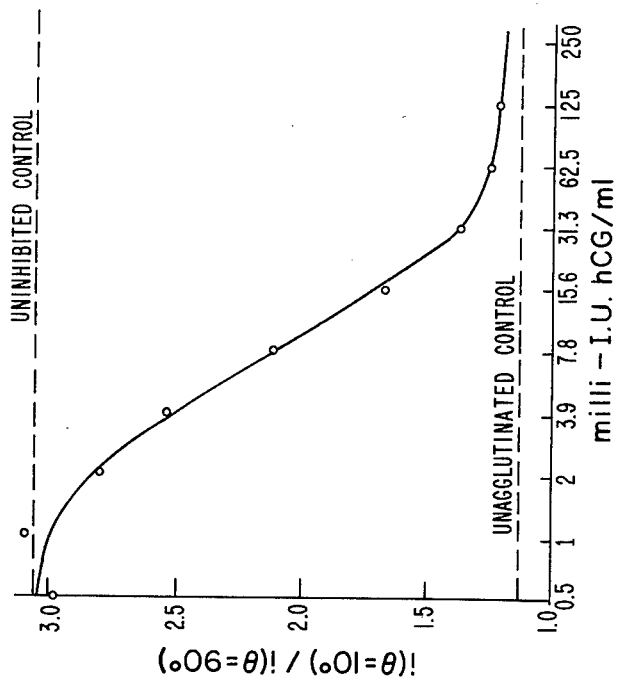
FIG. 3 is the agglutination inhibition curve. This is a plot of $i(10°)/i(90°)$ as a function of the concentration of inhibitor (hCG) measured in milli-International Units/ml. The agglutination concentration was fixed as described in the text. The dashed line labeled uninhibited control is the value of the anisotropy ratio corresponding to a sample containing no hCG as inhibitor.

In order to understand the present invention, it is believed useful to describe the physical effect utilized in the detection of the degree of agglutination. When a parallel beam of light impinges on a dielectric sphere of microscopic dimensions, a small amount of the beam power is removed and scattered in every direction. The actual way in which the scattered light is distributed as a function of the scattering angle depends on two numbers. The first number is the ratio of the index of refraction of the sphere to that of the surrounding fluid. For a given species in solution, this number is fixed. The second number is $\pi d/\lambda$, where d is the sphere's diameter and $\lambda$ is the wavelength of light in the medium. For our purposes, it is very instructive to briefly describe the changes that occur in the distribution of the scattered intensity as a function of angle when d is changed from values much smaller than $\lambda$ to values of the order of $\lambda$ or larger. It is convenient, but not necessary to consider the case where the incoming beam is vertically polarized and propagates in a horizontal plane, and the scattering angle is defined as the angle between the transmitted beam and the direction of observation, which also lies in the horizontal plane. At first, when d is much smaller than $\lambda$, the scattered intensity is very weak and isotropic; that is, no change in the scattered intensity can be noticed as a function of angle. If the particle size is made somewhat larger, but still d is much smaller than $\lambda$, the scattered intensity increases but remains isotropic.

A somewhat different situation is encountered when $\pi d/\lambda$ becomes comparable to unity. In this case, the intensity of the scattered light is peaked near the forward direction, and at first it decreases monotonically as a function of angle. If the particle diameter is made even larger, however, the scattered intensity at small angles will grow, but a minimum will develop at larger angles. The physical explanation for the occurence of such a minimum is that if the particle is large enough, the elementary wavelets radiated from different regions of the sphere will be able to interfere destructively. Consequently, it may occur that when the particle diameter increases beyond a given point, although the intensity scattered near the forward direction grows larger, the intensity scattered at an appreciably large angle (the angle where the minimum will develop) will actually decrease. Finally, if the particle diameter is made larger than the wavelength of light, then a complicated series of maxima and minima appears as a function of angle, the number, shape, and position of these lobular structures being a sensitive function of $\pi d/\lambda$.

During the early stages of an agglutination reaction, dimers and other low order complexes of carrier particles are formed. These complexes substantially alter the angular distribution of the scattered intensity since they act in effect like particles of larger diameter than the original carrier particles (monomers). By using carrier particles which are somewhat smaller in diameter than the light wavelength, the agglutination reaction product produces maximal changes in the anisotropy of the scattered light intensity. It is advantageous to utilize carrier particles having a size between about 0.07 microns and 2.0 microns. Preferably the quantity $\pi d/\lambda$ should lie in the range between 0.5 and 10. The light wavelength preferably should lie in the visible region. The carrier particles, preferably should be "monodisperse". In the method, we observe the change in anisotropy ratio associated with agglutination. It is therefore essential that the polydispersity of the coated unagglutinated sample produce a change in anisotropy ratio (relative to perfectly monodisperse) which is comparable to or less than the change in anistropy ratio associated with the smallest amount of agglutinator one wishes to detect reliably. Thus, it is desirable to utilize carrier particles that are as monodisperse as possible in order to maximize the sensitivity of this method. In the present state of the art, the coated unagglutinated sample typically contains about 10 percent by weight of carrier particle polymers which are predominantly dimers. With coated unagglutinated particles containing more than about 10 weight percent polymers, less sensitivity in the method is obtained. When coated unagglutinated particles containing less than about 10 weight percent polymers, greater sensitivity in the method is obtained. By properly choosing the scattering angles, the change in the anisotropy ratio can be maximized, for any particular carrier particle diameter, and independently of the concentration of carrier particles. The selection of optimal scattering angles is achieved by comparing the angular distribution of the scattered intensity in the case of unagglutinated carrier particles with the angular distribution obtained in the presence of a small amount of agglutinator. Optimal choice of scattering angles can be effected experimentally as follows: several dilutions of agglutinator are mixed with a fixed concentration of coated carrier particles, the agglutinator being chosen such that the state of the carrier particles varies from no agglutination to moderate agglutination for different samples. One sample serving as control contains no agglutinator. The scattered intensities $i(\theta)$ of the samples are then measured as a function of angle and finally the ratio $Q(\theta) = i(\theta) = i(\theta)/i_c(\theta)$, is plotted as a function of $\theta$ (i is the scattered intensity of the sample containing agglutinator and $i_c(\theta)$ is the intensity scattered from the control). The smaller the agglutinator concentration, the less agglutination occurs and, consequently, $i(\theta)$ for high dilutions approaches $i_c(\theta)$. Therefore, $Q(\theta)$ approaches 1 for all $\theta$ at high dilution. Based on these curves $Q(\theta)$, it is easy to identify the angles for which $R/R_c$ is either maximal or minimal. ($R_c$ is the anisotropy ratio of the control).

Since $$\frac{R(\theta_1,\theta_2)}{R_c(\theta_1,\theta_2)} = \frac{i(\theta_1)}{i(\theta_2)} \frac{i_c(\theta_2)}{i_c(\theta_1)} = \frac{Q(\theta_1)}{Q(\theta_2)},$$

we just determine at what angle $Q(\theta)$ is maximal and minimal respectively. These two positions determine the optimal scattering angles. Having maximized the sensitivity of the assay by proper choice of scattering angles, a standard agglutination curve is determined. This curve is a plot of the measured anisotropy ratio as a function of the concentration of the agglutinator to be assayed for. The agglutination curve is determined by measuring the intensity anisotropy ratio using, for example, successive dilutions of a standard sample of known concentration. The unknown agglutinator concentration is determined by a measurement of the anisotropy ratio produced by the unknown agglutinator and comparison with the standard agglutination curve.

In the process of this invention, an agglutination reaction is performed in any of the modes of operation described below. The agglutination reaction utilizing carrier particles may be used in four different modes to detect antigen or antibody as follows:

(1) With antigen-coated carrier particles as agglutinant and the complementary antibody as agglutinator.

(2) With antibody-coated carrier particles as agglutinant and the complementary antigen as agglutinator.

(3) The agglutination inhibition mode with antigen-coated spheres, wherein a fixed quantity of antibody is mixed with a dilution of the test sample containing the complementary antigen, inactivating a portion of the added antibody. In this case, the antigen contained in the test sample will be referred to as the inhibitor. This mixture then is combined with the antigen-coated carrier particles. The degree to which the antigen in the test sample inhibits the aggregation of the carrier particles, that would otherwise have occurred, indicates the concentration of antigen present.

(4) The agglutination inhibition mode with antibody-coated spheres wherein a fixed quantity of antigen is mixed with a dilution of the test sample containing the complementary antibody, inactivating a portion of the added antigen. In this case, the antibody contained in the sample will be referred to as the inhibitor. This mixture then is combined with the antibody-coated carrier particles. The degree to which the antibody present in the sample inhibits the aggregation of carrier particles, which would otherwise have occurred, indicates the concentration of antibody present.

In modes 1 and 4, the agglutination reaction serves as an antibody assay. In modes 2 and 3, it serves as an antigen assay. Mode 3 is of particular practical importance as an antigen assay, since it is generally easier to obtain a sufficient quantity of purified antigen to coat the carrier particles than to obtain a similar quantity of complementary antibody. Moreover, in mode 3, the agglutination reaction serves to detect antigen molecules of any size with one or more haptenic sites. On the other hand, in mode 2, the agglutination reaction serves to detect only polyhaptenic antigens, which are of sufficient size (on the order of 100 Å in diameter) to effect crosslinking of the carrier particles.

In addition to determining antigen and antibody concentrations, the process of this invention can be used to determine the concentration of any substance capable of specifically promoting or inhibiting an agglutination reaction even where the formation of antigen-antibody bonds may not be involved in the agglutination process.

In the two direct modes (1) and (2), the standard curve is a graph of the anisotropy ratio R as a function of agglutinator concentration. In the two inhibition modes (3) and (4), the standard curve is a graph of R as a function of inhibitor concentration. The standard agglutination curve will be either a monotonic or non-monotonic function of the agglutinator or inhibitor concentration. In the case where the anisotropy ratio R is a monotonic function of the agglutinator or inhibitor concentration, the standard curve will have a region of non zero slope corresponding to a limited range of agglutinator or inhibitor concentrations. We shall refer to this range as the concentration window. In this monotonic case, a single measurement of R for an unknown sample serves to determine unambiguously that the concentration of agglutinator or inhibitor in the sample is greater, less than, or within the range of the concentration window. In the case of a non-monotonic standard curve, measurements at two or perhaps more dilutions of an unknown sample may be necessary to obtain the same information. In either the monotonic or non-monotonic case, the known dilutions of the original sample must result in an agglutinator or inhibitor concentration lying within the concentration window in order to make a quantitative determination of the original agglutinator or inhibitor concentration.

The choice of agglutinator concentration in the inhibition mode assay involves the following considerations. The choice of agglutinator concentration determines both the width and location of the window within which inhibitor concentrations can be determined quantitatively. Agglutinator concentrations which produce only slight changes in R allow the detection of very small inhibitor concentrations. However, under these conditions, a narrow inhibitor concentration window is produced. On the other hand, if a larger agglutinator concentration is chosen (resulting in strong agglutination and a large change in R), the assay will have a larger window, but is not maximally sensitive, since small amounts of inhibitor will block only a small fraction of the agglutinator. The sensitivity of R to small changes in inhibitor concentration will be correspondingly reduced. Thus, the provision of a wide window, while facilitating quantitative determination of the unknown inhibitor concentration, reduces the sensitivity of the assay. Choice of the agglutinator concentration to be used in any particular assay application depends in detail upon the information desired and the accuracy with which the apparatus can be used to detect small changes in R.

The process of this invention provides substantial advantages over the processes of the prior art. The process does not require that the agglutination reaction be conducted at such a high concentration of agglutinator that macroscopic precipitation of the agglutination reaction product occurs. Thus, the method of this invention can be used to measure the much lower antigen or antibody concentrations associated with the microscopic reversible stages of the agglutination reaction. This stage may involve the dimerizing of the carrier particles whereas the macroscopically visible agglutinate may contain hundreds of thousands of carrier particles. In the example discussed below, no macroscopic agglutination occurred. The conventional detection method (observation of visible clumping of the carrier particles) permits the detection of 0.05 $\mu$g/ml antigen or more; whereas the process of this invention can detect as little as $1 \times 10^{-4}$ $\mu$g/ml, or about $5 \times 10^{-12}$ moles/ml, of antigen. Moreover, in the process of this invention, the agglutination reaction may be performed in volumes as small as 100 microliters. Moreover, in the process of this invention, the degree of agglutination is quantitatively measured at the microscopic, reversible and reproducible stage of the agglutination reaction. Thus, this process serves to transform the agglutination reaction from a rough qualitative measure of antigen or antibody concentration to an accurate, reproducible means of quantitating antibody or antigen concentration. In the present invention, by using carrier particles and taking the ratio of the intensity scattered at two different angles, we look at a strong effect which is less prone to be obscured by unavoidable imperfections in the sample. Indeed, the process of this invention is able to detect about $2 \times 10^{-3}$ I.U. hCG/ml in urine, for example, which is about a factor of 500 more sensitive than slide or tube agglutination tests for the same system (sensitivity $\sim 1 \times 10^3$ I.U. hCG/ml). Furthermore, the present invention allows the performance of the sophisticated form of agglutination inhibition test, which in principle permits one to assay for any conceivable immunogenic molecule, in contrast to the direct mode assay.

The process of this invention is applicable for accurately determining the concentration of any antigen or antibody capable of promoting or inhibiting an agglutination reaction. Representative suitable antigens or antibodies that can be tested include hormones such as human chorionic gonadotropin which can be detected accurately to concentrations as low as $2 \times 10^{-3}$ International Units with rabbit antisera in mode 3, luteinizing hormone, insulin, parathyroid hormone, drugs such as digoxin, barbiturates and diphenylhydantoin, and tumor and virus associated antigens or antibodies including Hepatitis-associated antigen and Carcino-Embryonic antigen. Thus, the process of this invention provides a means for measuring a very wide range of antigens and antibodies of research and clinical importance. For example, the process of this invention provides an accurate means for testing for stimulation of ovulation (luteinizing hormone) and for normal and ectopic pregnancy (human chorionic gonadotropin).

Apparatus suitable for carrying out the process of this invention comprises a monochromatic beam of light from a source such as a laser with reduced spatial coherence, or conventional light source with narrow band filters slightly focused by a lens onto a sample which contains the suspension of carrier particles to be studied. The light scattered in two directions, e.g., the 10° and the 90° direction, is collected using suitable optical systems. The ratio of the intensities of the light collected by the two optical systems can be measured using any suitable detector. The actual intensities measured depend not only on the scattering angles and the degree of agglutination of the sample, but also on the optical systems used to collect the light.

EXAMPLE I

This example illustrates the process of this invention in mode 3, as applied to the case that the antigen is human chorionic gonadotropin (hCG) coated on carrier particles consisting of polystyrene latex spheres of diameter 2515 Å, having a polydispersity in diameter of less than about 20%. The agglutinator consisted of rabbit antisera to human hCG. Varying quantities of hCG were used to inhibit the agglutination of the hCG coated spheres by the rabbit antibody.

Figure 1:
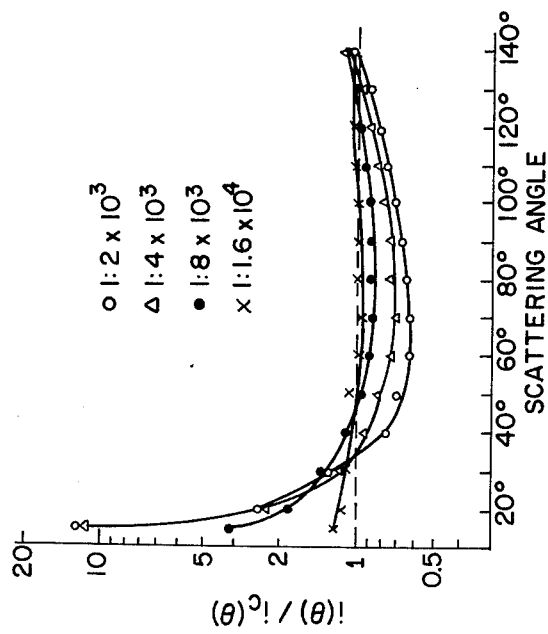
FIG. 1 is a plot of the ratio $i(\theta)/i_c(\theta)$ versus scattering angle $\theta$, for samples containing various dilutions of agglutinator. $i_c(\theta)$ is the intensity of light scattered through an angle $\theta$ by a control sample containing no agglutinator, and $i(\theta)$ is the intensity of light scattered through an angle $\theta$ by a sample containing a fixed dilution of agglutinator. The antisera dilution factors for each curve are shown in the drawing.

In order to demonstrate the sensitivity of this technique, we established a standard inhibition curve using known concentrations of the inhibitor hCG. To produce the standard curve the following steps were taken:

(1) The scattering angles $\theta_1$ and $\theta_2$ were chosen to optimize the detectibility of changes in the anisotropy ratio caused by small quantities of agglutinator. The optimization procedure consisted of the following steps: Samples were prepared containing various dilutions of the original rabbit antisera and a fixed concentration (16 $\mu$g/ml) of hCG coated carrier particles, in 0.01 M Tris buffer at pH 8.0 and 0.15 M NaCl. The dilutions ranged from a factor of 20,000 to a factor of 1,280,000 resulting in four different samples each containing a different concentration of antisera. After incubation at room temperature for 18 hours, the angular dependence of the intensity of the light scattered from each sample $i(\theta)$ was measured for angles ranging from 15° to 140°. Similar intensity measurements versus angle $i_c(\theta)$ were made for a control sample containing no agglutinator. Plots of $i(\theta)/i_c(\theta)$ as a function of scattering angle were then constructed for each sample. (See FIG. 1). From these plots, it was determined that one angle should be less than or equal to 15° and the other should be between 60° and 90° in order to optimize the sensitivity of the assay. The optimal scattering angles depend primarily on the size of the carrier particles and not upon their concentration. Consequently, the optimization procedure need be carried out only once for any particular size carrier particle. For the present assay, we chose the scattering angles to be 10° and 90°, respectively.

Figure 2:
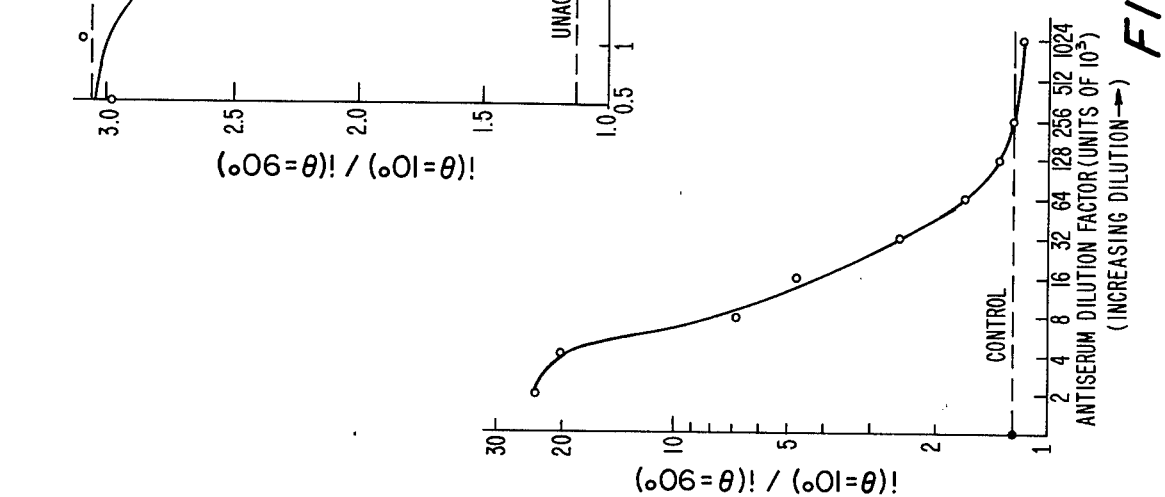
FIG. 2 is a plot of $i(10°)/i(90°)$ as a function of the factor by which the original rabbit antisera is diluted in units of $10^3$. That is, 2 corresponds to dilution by a factor 2000, 4, dilution by a factor 4000, etc.

(2) A suitable concentration of agglutinator to be inhibited by the hCG was determined as follows: An agglutination curve, i.e., a plot of $R = i(10°)/i(90°)$ as a function of the degree of dilution of the rabbit antisera was obtained using a fixed concentration (16 $\mu$g/ml) of hCG coated latex particles suspended in urine at pH 8.2 (filtered through a 0.2 filter). From the agglutination curve presented in FIG. 2, one notes that antisera dilutions of less than 4000 strongly agglutinate the carrier particles, resulting in values of R which are approximately 20 times larger than that observed for the unagglutinated (control) sample. For higher dilutions of antisera, decreasing agglutination leads to smaller values of R. The highest dilution resulting in a detectable change in R was 128,000. If the absolute concentration of antibodies in the antisera were known, this curve would represent a standard curve for a direct mode antibody assay (mode 1) and the highest dilution producing a detectable change in R from its control value $R_c$ would determine the sensitivity limit. Based on the results obtained, an agglutinator concentration resulting from dilution by a factor of 22,000 was chosen, yielding an R which is about a factor of 3 larger than $R_c$. Although this probably does not give the highest sensitivity possible, this choice of agglutinator concentration resulted in a change in R large compared to the instrumental sensitivity for the measurement of R.

(3) A standard inhibition curve was next obtained using the fixed dilution (22,000) of rabbit antisera. Varying known amounts of hCG were used to inhibit the rabbit antisera. The known concentrations of hCG were abtained by serially diluting a sample of known concentration of hCG obtained from the Serono Co. of Boston. The resulting standard inhibition curve is presented in FIG. 3 where we plot R as a function of the known concentration of inhibitor. From this figure, we see that a concentration of hCG as small as $2 \times 10^{-3}$ I.U./ml can be clearly detected. This sensitivity is at least 200 times greater than the conventionally used slide or tube agglutination test. In fact, the present sensitivity is only a factor of 2 less than that obtained using radio immunoassays ($\sim 1 \times 10^{-3}$ I.U. hCG/ml).

We claim:

1. The process for determining the concentration of a substance which promotes or inhibits an agglutination reaction including an agglutinant coated on carrier particles which comprises:

(a) preparing a plurality of samples by mixing a known concentration of an agglutinant coated on a carrier with either known varying concentrations of the agglutinator or with a mixture of a fixed concentration of the agglutinator with varying concentrations of an agglutination inhibitor, said carrier having a particle size between about 0.07 and 2 microns and a poly-dispersity in diameter of less than about 20%, exposing an agglutinated reaction product of said agglutinant and an agglutinator to a beam of essentially monochromatic light, measuring the intensity of scattered light due to each of said reaction products at two different angles, said angles being the same for each reaction product and determining the quantitative relationship between the ratio of the intensity of scattered light by said agglutinated reaction products at said two angles thereby to establish a standard agglutination curve that relates agglutinator concentration or agglutinant concentration with the ratio of the intensity of scattered light at said two angles, (b) mixing either a fixed concentration of the agglutinant coated on the carrier or a mixture of a fixed concentration of the agglutinant coated on the carrier and a fixed concentration of the agglutinant in solution with one or more dilutions of the substance being tested, said substance acting either as an agglutinant or as an inhibitor to form at least one agglutinated reaction product of the dilutions, (c) determining the ratio of the intensity of the scattered light at said two angles by the agglutinated reaction product of the dilutions of the substance being tested, (d) comparing the ratio of the scattered light intensity of the agglutinated reaction product obtained in step (c) with the quantitative relationship determined by step (a) thereby to determine the concentration of the substance being tested from said standard agglutination curve.

2. The process of claim 1 wherein the agglutinant comprises antigen-coated carrier particles.

3. The process of claim 1 wherein the agglutinant comprises antibody-coated carrier particles.

4. The process of claim 1 wherein the substance being tested is an antigen or a hapten which first is mixed with a fixed concentration of its complementary antibody and combining the resultant mixture with a fixed concentration of antigen-coated carrier particles.

5. The process of claim 1 wherein the substance being tested is an antibody which first is mixed with a fixed concentration of its complementary antigen and combining the resultant mixture with a fixed concentration of antibody-coated carrier particles.

* * * * *